(12) United States Patent
Shin

(10) Patent No.: US 11,191,526 B2
(45) Date of Patent: Dec. 7, 2021

(54) ULTRASOUND DIAGNOSIS APPARATUS AND METHOD OF CONTROLLING THE SAME

(71) Applicant: SAMSUNG MEDISON CO., LTD., Hongcheon-gun (KR)

(72) Inventor: Dong-kuk Shin, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 498 days.

(21) Appl. No.: 16/148,559

(22) Filed: Oct. 1, 2018

(65) Prior Publication Data

US 2019/0239858 A1 Aug. 8, 2019

(30) Foreign Application Priority Data

Feb. 6, 2018 (KR) ........................ 10-2018-0014714

(51) Int. Cl.
*G06K 9/00* (2006.01)
*A61B 8/08* (2006.01)
(Continued)

(52) U.S. Cl.
CPC ............ *A61B 8/5253* (2013.01); *A61B 8/463* (2013.01); *A61B 8/466* (2013.01); *A61B 8/469* (2013.01);
(Continued)

(58) Field of Classification Search
CPC ......... A61B 8/461; A61B 8/463; A61B 8/466; A61B 8/469; A61B 8/483; A61B 8/523;
(Continued)

(56) References Cited

U.S. PATENT DOCUMENTS 8,938,113 B2  1/2015  Kovalan et al.
9,865,059 B2  1/2018  Gulaka et al.
(Continued)

FOREIGN PATENT DOCUMENTS

JP  2004-174220 A  6/2004
JP  2011-160962 A  8/2011
(Continued)

OTHER PUBLICATIONS

Communication dated Jun. 6, 2019 issued by the European Intellectual Property Office in counterpart European Application No. 18206979.9.

*Primary Examiner* — Avinash Yentrapati
(74) *Attorney, Agent, or Firm* — Sughrue Mion, PLLC

(57) ABSTRACT

Provided is an ultrasound diagnosis apparatus configured to automatically search a cross-section including a desired feature of an object. The ultrasound diagnosis apparatus includes: a display; a memory storing one or more instructions; and at least one processor configured to execute the stored one or more instructions to: acquire three-dimensional (3D) ultrasound volume data regarding a region of interest of an object; identify a plurality of two-dimensional (2D) cross-sections, each including at least one feature to be observed, based on the 3D ultrasound volume data; determine priority levels of the plurality of 2D cross-sections based on the at least one feature included in each of the plurality of 2D cross-sections; and control the display to display a plurality of 2D ultrasound images respectively corresponding to at least some of the plurality of 2D cross-sections based on the priority levels.

22 Claims, 19 Drawing Sheets

(51) Int. Cl.
    *G06T 7/00*               (2017.01)
    *A61B 8/00*            (2006.01)

(52) U.S. Cl.
    CPC .............. *A61B 8/483* (2013.01); *A61B 8/523* (2013.01); *A61B 8/54* (2013.01); *G06T 7/00* (2013.01); *G06T 7/0012* (2013.01); *A61B 8/461* (2013.01)

(58) Field of Classification Search
    CPC ........... A61B 8/5253; A61B 8/54; G06T 7/00; G06T 7/0012
    See application file for complete search history.

(56) References Cited

U.S. PATENT DOCUMENTS

| | | | | |
|---|---|---|---|---|
| 2006/0228012 | A1* | 10/2006 | Masuzawa | G06T 19/00 382/131 |
| 2009/0129642 | A1* | 5/2009 | Matsumoto | G06T 5/50 382/128 |
| 2013/0012820 | A1* | 1/2013 | Brown | A61B 8/466 600/443 |
| 2013/0018264 | A1 | 1/2013 | Gerard et al. | |
| 2013/0121548 | A1* | 5/2013 | Kovalan | G06N 3/086 382/128 |
| 2016/0125607 | A1* | 5/2016 | Gulaka | G06T 7/74 382/128 |
| 2016/0157832 | A1* | 6/2016 | Kang | A61B 8/5223 600/443 |
| 2016/0331349 | A1 | 11/2016 | Abe | |
| 2016/0334964 | A1* | 11/2016 | Jeon | G16H 30/40 |
| 2017/0046485 | A1* | 2/2017 | Reicher | G06K 9/6267 |
| 2017/0215838 | A1* | 8/2017 | Park | A61B 8/463 |

FOREIGN PATENT DOCUMENTS

| | | |
|---|---|---|
| JP | 2016-214393 A | 12/2016 |
| KR | 10-1636876 B1 | 7/2016 |
| KR | 10-2017-0047423 A | 5/2017 |
| WO | 2011/117788 A1 | 9/2011 |

\* cited by examiner

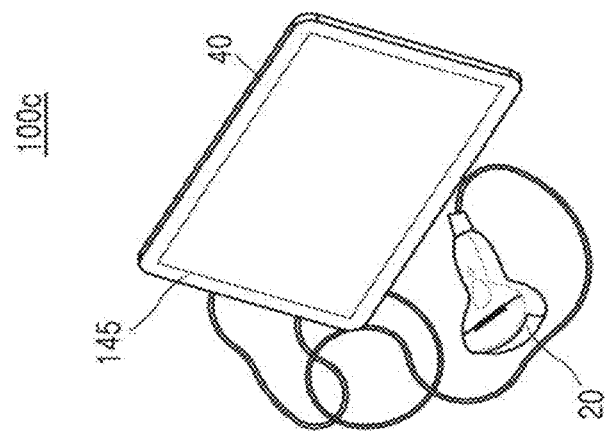
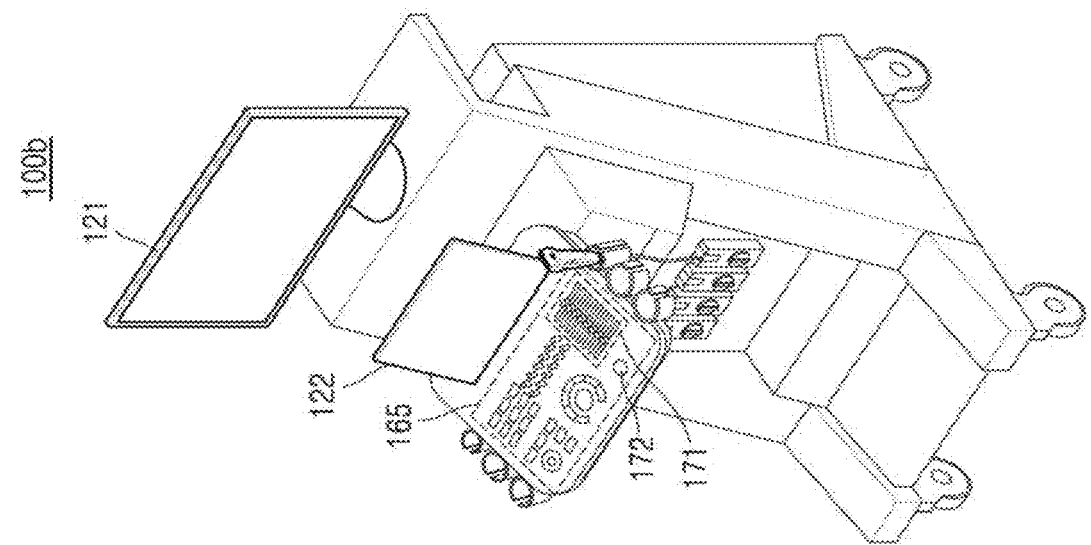
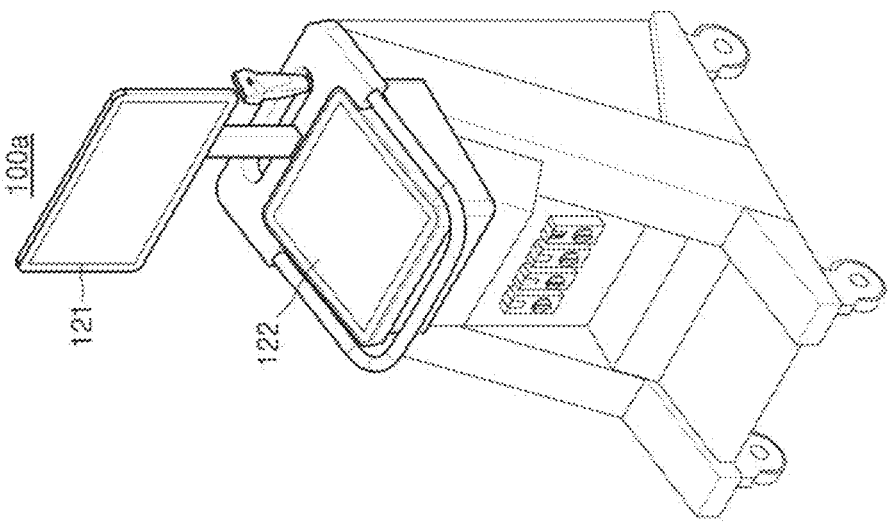

FIG. 8
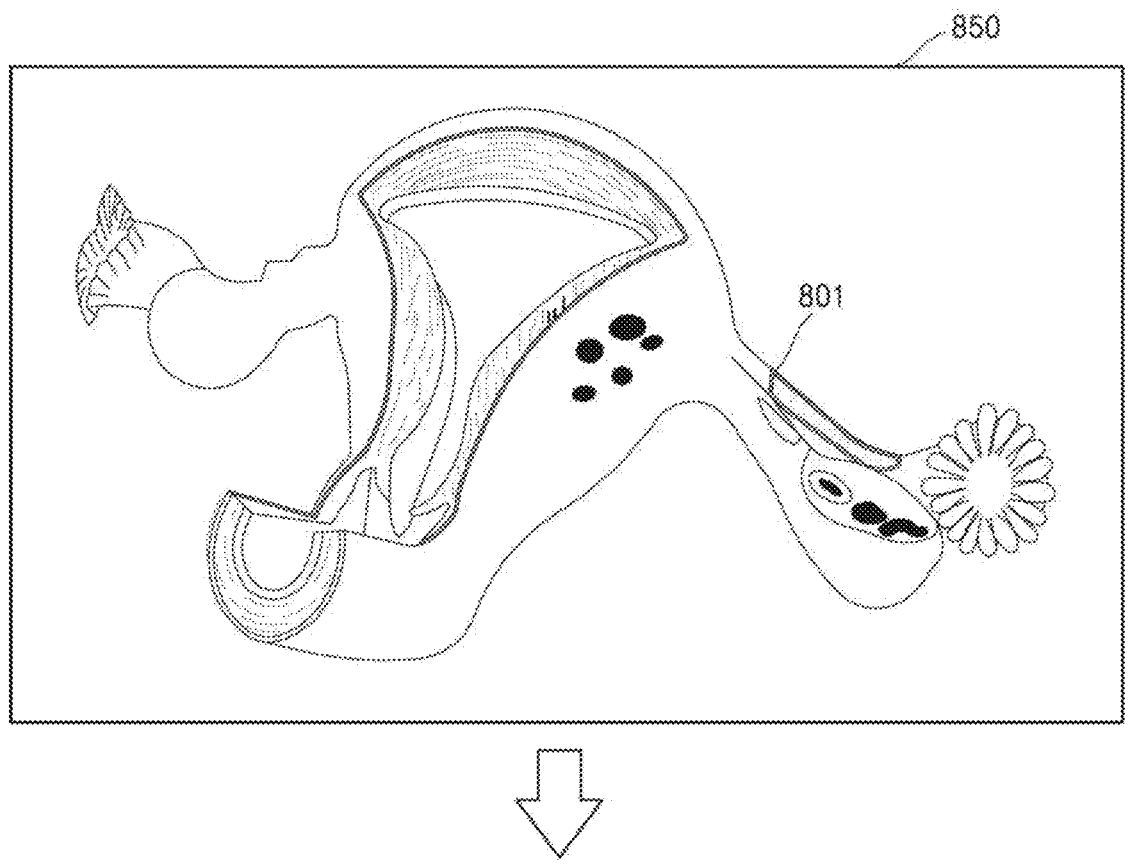
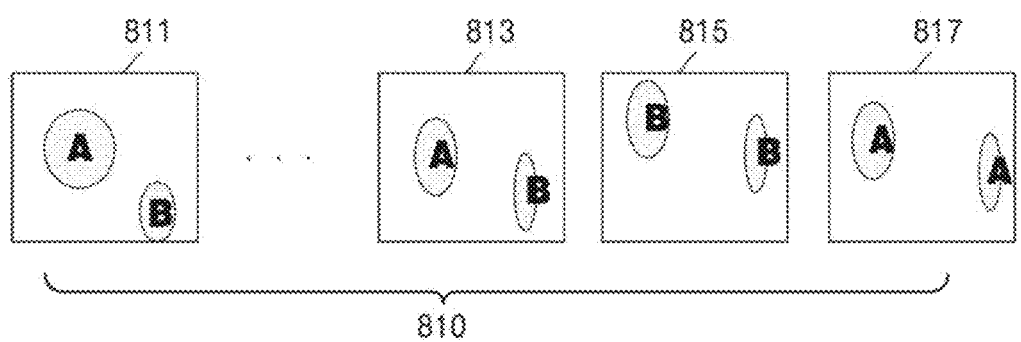

FIG. 9A
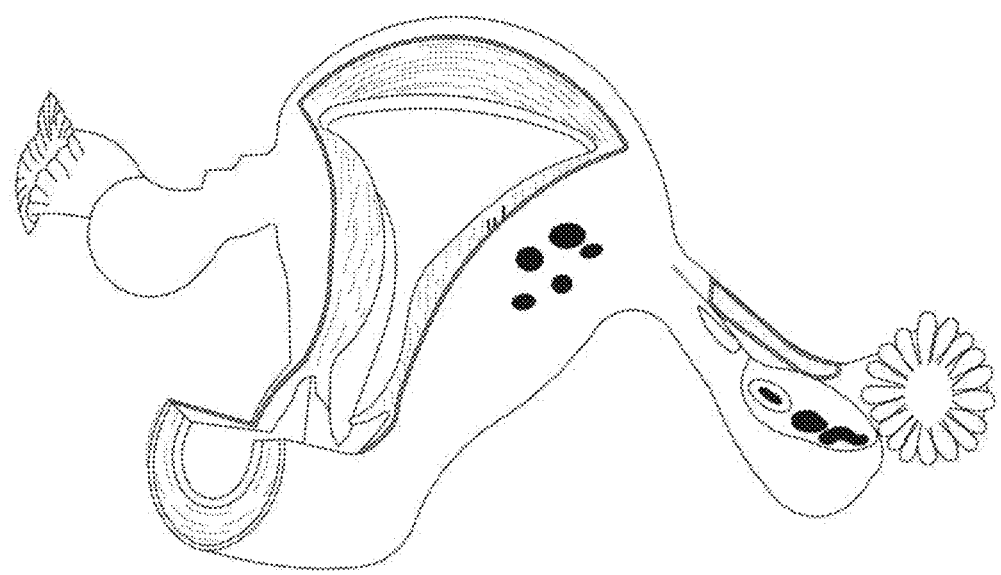
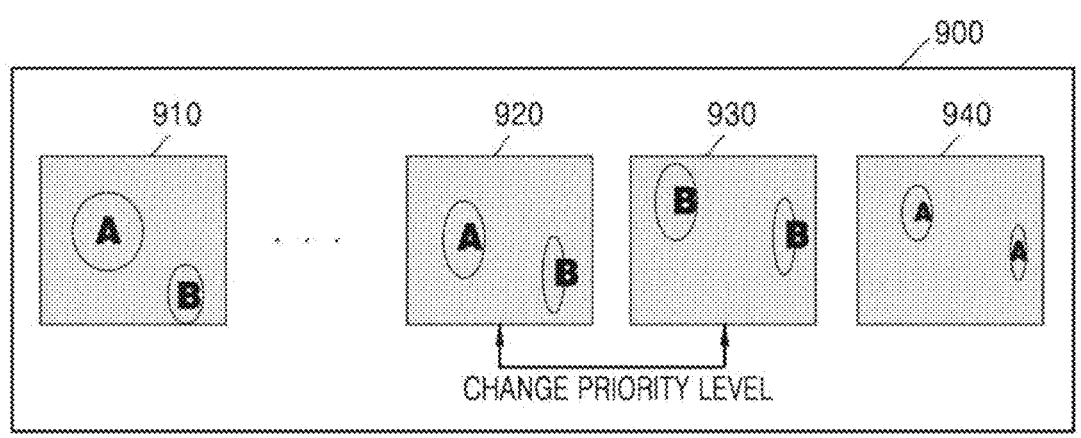

FIG. 9B
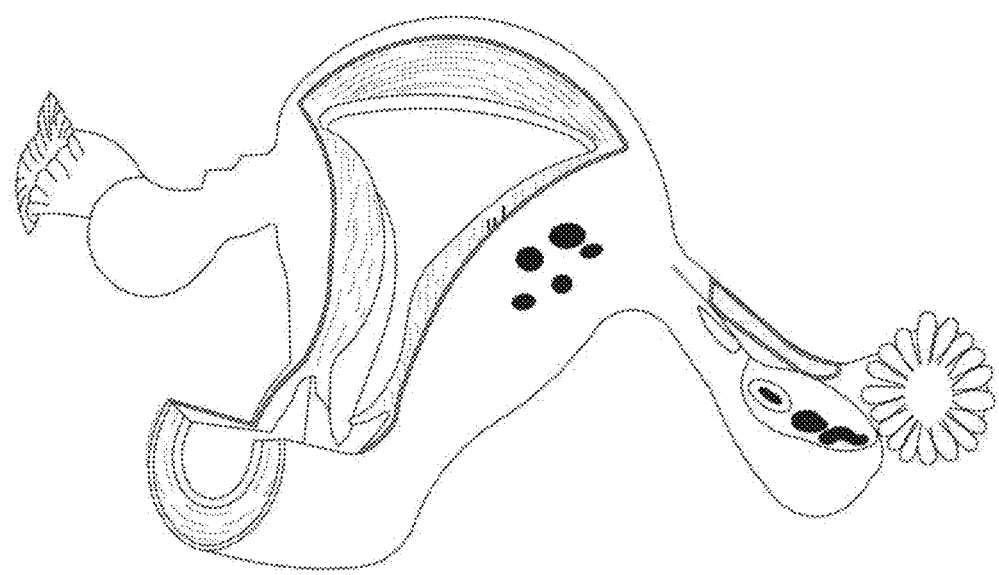
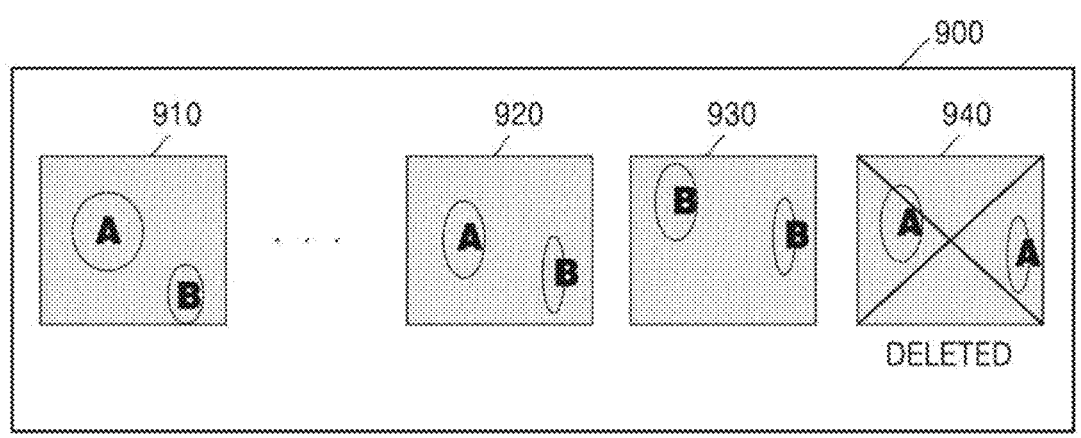

FIG. 10A
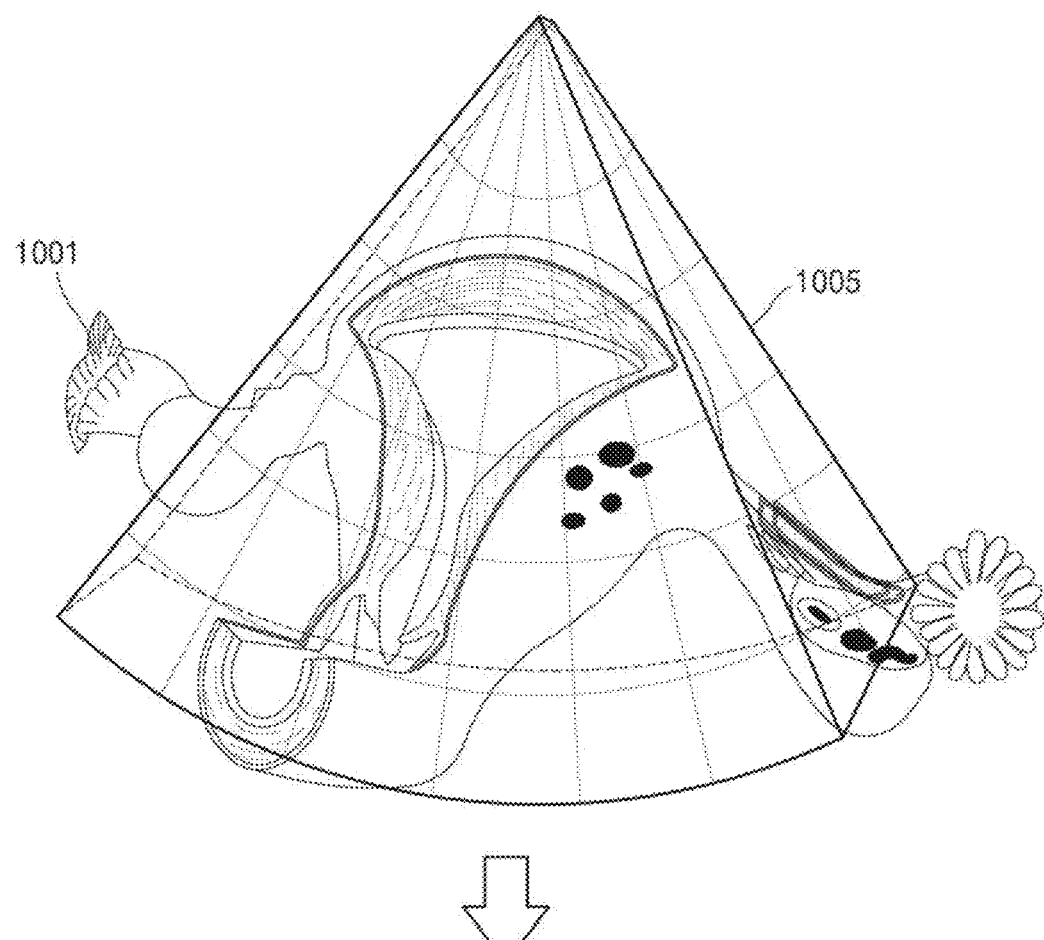
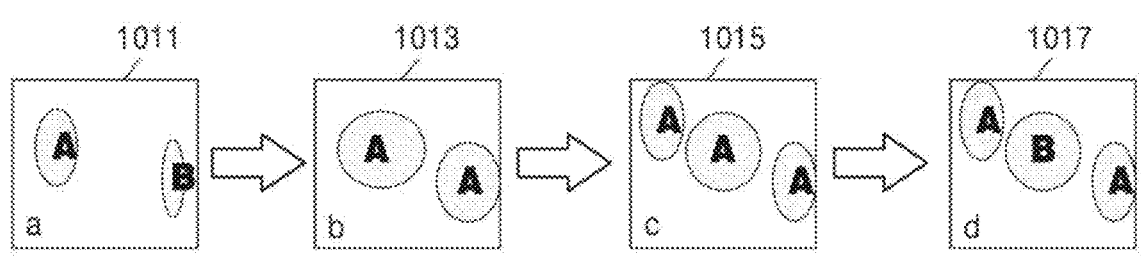
ORDER OF IDENTIFYING 2D CROSS-SECTIONS

UPDATE PLURALITY OF 2D IMAGES IN REAL-TIME

UPDATE PLURALITY OF 2D IMAGES IN REAL-TIME

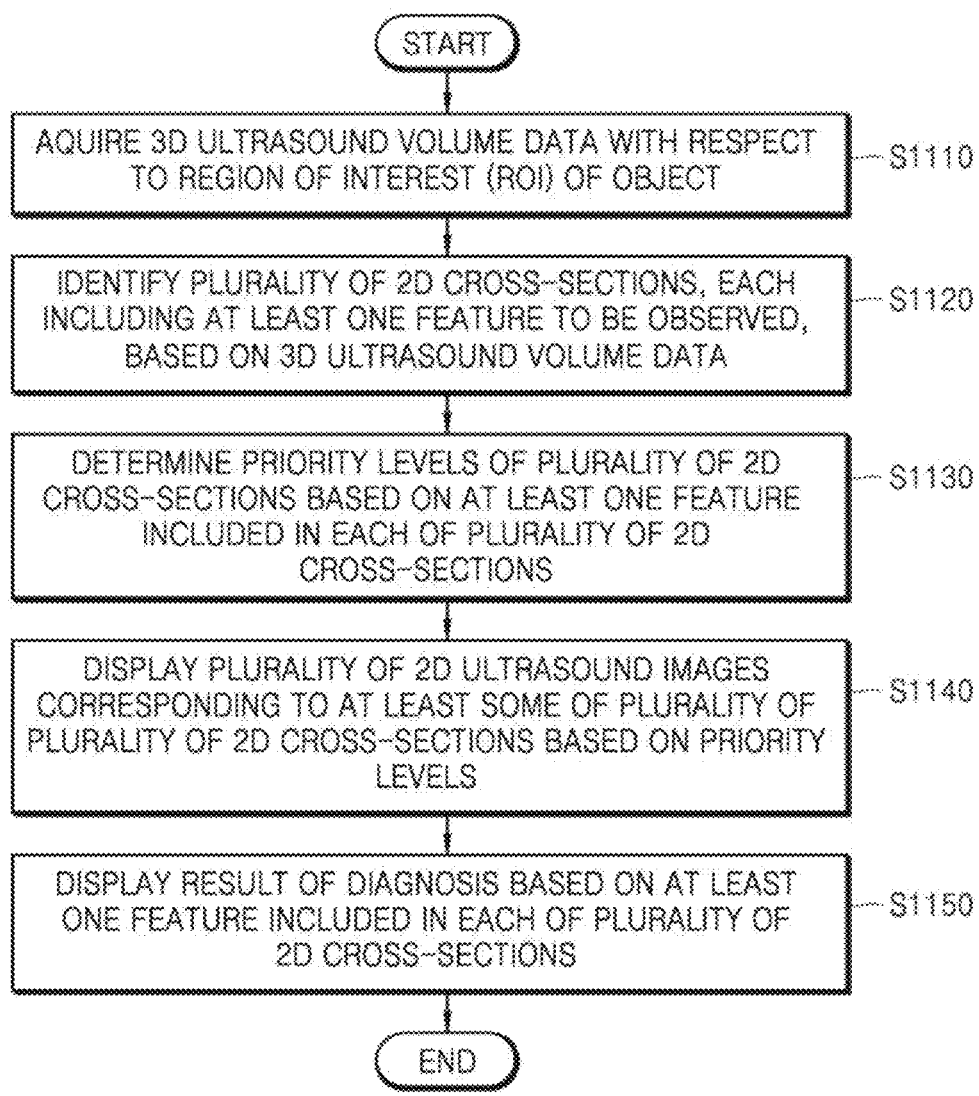

ULTRASOUND DIAGNOSIS APPARATUS AND METHOD OF CONTROLLING THE SAME

CROSS-REFERENCE TO RELATED APPLICATION(S)

This application is based on and claims priority under 35 U.S.C. § 119 to Korean Patent Application No. 10-2018-0014714, filed on Feb. 6, 2018, in the Korean Intellectual Property Office, the disclosure of which is incorporated by reference herein in its entirety.

BACKGROUND

1. Field

The disclosure relates to ultrasound diagnosis apparatuses and methods of controlling the same, and more particularly, to ultrasound diagnosis apparatuses capable of automatically searching for a cross-section including a desired feature of an object and methods of controlling the ultrasound diagnosis apparatuses.

2. Description of Related Art

Recently, in the medical field, various types of medical imaging apparatuses have been widely used to visualize and acquire information about a living tissue of a human body for early diagnosis or surgery with regard to various diseases. Representative examples of these medical imaging apparatuses may include an ultrasound diagnosis apparatus, a computed tomography (CT) apparatus, and a magnetic resonance imaging (MRI) apparatus.

Ultrasound diagnosis apparatuses transmit ultrasound signals generated by transducers of a probe to an object and receive information of signals reflected from the object, thereby obtaining at least one image of an internal part (e.g., soft tissues or blood flow) of the object. In particular, ultrasound diagnosis apparatuses are used for medical purposes including observing an internal area of an object, detecting foreign substances, and assessing injuries. Such ultrasound diagnosis apparatuses exhibit high stability, display images in real-time, and are safe due to lack of radiation exposure compared to diagnostic X-ray apparatuses. Therefore, ultrasound diagnosis apparatuses have been widely used together with other types of imaging diagnosis apparatuses.

In addition, volume data that represents a volume of a three-dimensional (3D) object is acquired by the ultrasound diagnosis apparatus, etc. and is displayed as visual information useful for diagnosis, which is referred to as volume rendering. This volume rendering technique allows generation of a 2D ultrasound image corresponding to a desired cross-section by using the acquired 3D volume data with respect to the object.

According to the related art, when a user selects a desired cross-section in a region of interest (ROI) and an ultrasound diagnosis apparatus displays an image of the selected cross-section, the user is able to simply identify a lesion of an object by examining the displayed image.

SUMMARY

Provided are ultrasound diagnosis apparatuses and methods of controlling the ultrasound diagnosis apparatuses, whereby cross-sections including features to be observed may be automatically detected by examining various views and two-dimensional (2D) ultrasound images respectively corresponding to the detected cross-sections may be displayed according to their priority levels.

Provided are ultrasound diagnosis apparatuses and methods of controlling the ultrasound diagnosis apparatuses, whereby a cross-section including a feature to be observed may be automatically detected and then an object may be diagnosed based on the detected cross-section.

Additional aspects will be set forth in part in the description which follows and, in part, will be apparent from the description, or may be learned by practice of the presented embodiments.

In accordance with an aspect of the disclosure, an ultrasound diagnosis apparatus includes: a display; a memory storing one or more instructions; and at least one processor configured to execute the stored one or more instructions to acquire three-dimensional (3D) ultrasound volume data regarding a region of interest of an object, identify a plurality of 2D cross-sections, each including at least one feature to be observed, based on the 3D ultrasound volume data, determine priority levels of the plurality of 2D cross-sections based on the at least one feature included in each of the plurality of 2D cross-sections, and control the display to display a plurality of 2D ultrasound images respectively corresponding to at least some of the plurality of 2D cross-sections based on the priority levels.

The at least one processor may be further configured to execute the stored one or more instructions to control the display to display the plurality of 2D ultrasound images in a descending order of the priority levels.

The at least one processor may be further configured to execute the stored one or more instructions to change, based on a user input, an order in which the plurality of 2D ultrasound images are displayed.

The at least one processor may be further configured to execute the stored one or more instructions to determine, based on a user input, an ultrasound image that is not to be displayed from among the plurality of 2D ultrasound images.

The plurality of 2D cross-sections may be acquired by searching cross-sections respectively perpendicular to a first axis, a second axis, and a third axis with respect to the 3D ultrasound volume data regarding the region of interest, and the first through third axes may be orthogonal to one another.

The plurality of 2D cross-sections may be acquired by searching cross-sections respectively parallel to a first axis, a second axis, and a third axis with respect to the 3D ultrasound volume data regarding the region of interest, and the first through third axes may be orthogonal to one another.

The determining of the priority levels of the plurality of 2D cross-sections may include acquiring an area and a number of portions including the at least one feature in each of the plurality of 2D cross-sections and determining the priority levels of the plurality of 2D cross-sections based on at least one of the area and the number.

The at least one feature to be observed may include at least one of a shape, a texture, a propensity, and a characteristic portion of a tissue in the region of interest.

The at least one processor may be further configured to execute the stored one or more instructions to determine at least one feature to be observed based on a user input.

The at least one feature to be observed may include a plurality of features respectively having predetermined weight values, and the at least one processor may be further configured to execute the stored one or more instructions to determine the priority levels of the plurality of 2D cross-sections based on the plurality of features to which the predetermined weight values are respectively applied.

The at least one processor may be further configured to execute the stored one or more instructions to update the priority levels of the plurality of 2D cross-sections based on the at least one feature while respectively identifying the plurality of 2D cross-sections and control the display to display the plurality of 2D ultrasound images respectively corresponding to at least some of the plurality of 2D cross-sections based on the updated priority levels.

The at least one processor may be further configured to execute the stored one or more instructions to control the display to display a result of diagnosis based on the at least one feature included in each of the plurality of 2D cross-sections.

The at least one processor may be further configured to execute the stored one or more instructions to control the display to display a 3D ultrasound image obtained based on the 3D ultrasound volume data, together with the plurality of 2D ultrasound images and control the display to display cross-sections corresponding to the plurality of 2D ultrasound images in the 3D image.

In accordance with another aspect of the disclosure, a method of controlling an ultrasound diagnosis apparatus includes: acquiring 3D ultrasound volume data regarding a region of interest of an object; identifying a plurality 2D cross-sections, each including at least one feature to be observed, based on the 3D ultrasound volume data;

determining priority levels of the plurality of 2D cross-sections based on the at least one feature included in each of the plurality of 2D cross-sections; and displaying a plurality of 2D ultrasound images respectively corresponding to at least some of the plurality of 2D cross-sections based on the priority levels.

In accordance with another aspect of the disclosure, a computer program product includes a non-transitory computer-readable recording medium having recorded thereon a program for executing a method of controlling an ultrasound diagnosis apparatus on a computer.

In accordance with another aspect of the disclosure, an ultrasound diagnosis apparatus includes: a display; a memory storing one or more instructions; and at least one processor configured to execute the stored one or more instructions to acquire ultrasound image data regarding a region of interest of an object, identify a first cross-section including at least one feature to be observed based on the ultrasound image data, determine a priority level of the first cross-section based on the at least one feature included in the first cross-section and at least one feature in each of at least one previously identified cross-section, and control the display to display, based on the priority level, a plurality of 2D ultrasound images respectively corresponding to at least some of the first cross-section and the at least one previously identified cross-section.

The at least one processor may be further configured to execute the stored one or more instructions to acquire 3D ultrasound volume data based on the ultrasound image data and control the display to display a 3D ultrasound image obtained based on the 3D ultrasound volume data.

BRIEF DESCRIPTION OF THE DRAWINGS

The above and other aspects, features, and advantages of certain embodiments of the present disclosure will be more apparent from the following description taken in conjunction with the accompanying drawings, in which:

FIGS. 2A, 2B, and 2C are diagrams respectively illustrating an ultrasound diagnosis apparatus according to an embodiment;

FIG. 8 is a diagram for explaining an example in which an ultrasound diagnosis apparatus determines a priority level of a plurality of 2D cross-sections based on at least one feature included therein, according to an embodiment;

FIGS. 9A and 9B are diagrams for explaining an example in which an ultrasound diagnosis apparatus displays a plurality of 2D ultrasound images respectively corresponding to at least some of a plurality of 2D cross-sections based on their priority levels, according to an embodiment;

FIGS. 10A through 10E are diagrams for explaining an example in which an ultrasound diagnosis apparatus displays a 2D ultrasound image in real-time while identifying a cross-section including at least one feature to be observed, according to an embodiment;

FIG. 11 is a flowchart of a method of controlling an ultrasound diagnosis apparatus, according to an embodiment.

DETAILED DESCRIPTION

Figure 1:
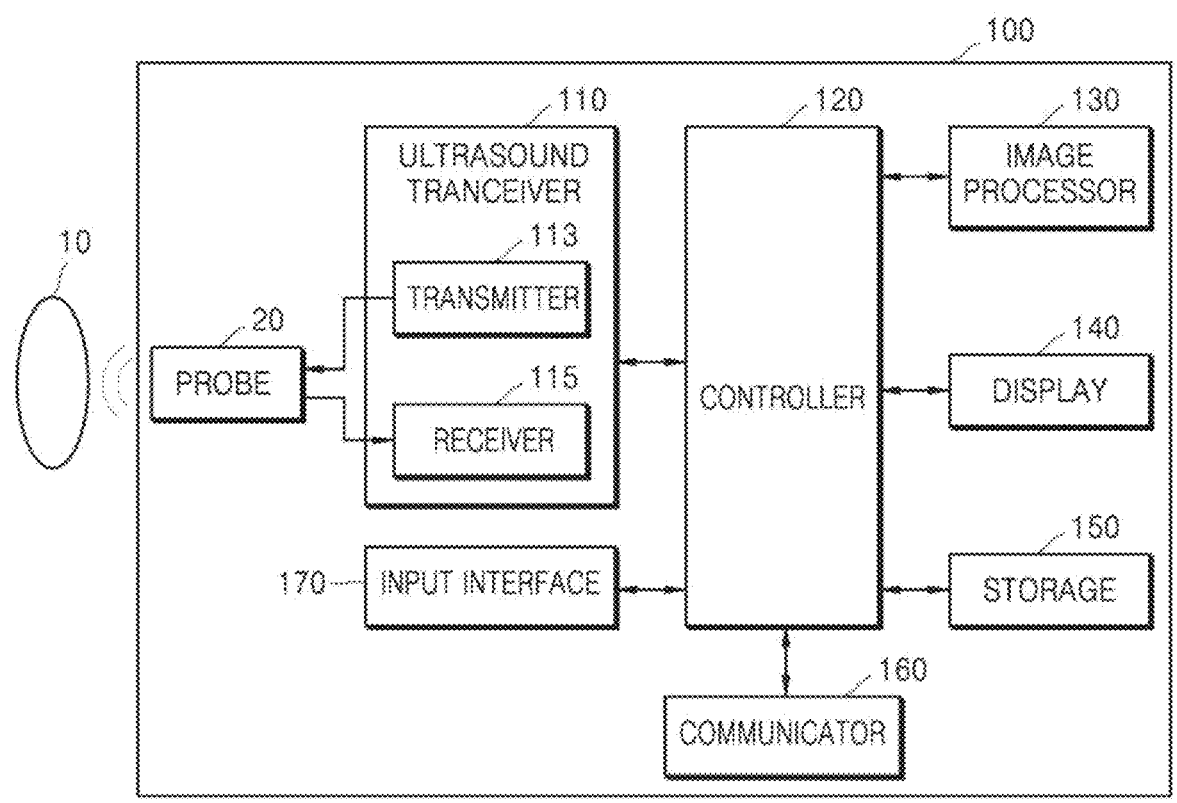
FIG. 1 is a block diagram illustrating an ultrasound diagnosis apparatus according to an embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

In the following description, the same drawing reference numerals are used for the same elements even in different drawings. The matters defined in the description, such as detailed construction and elements, are provided to assist in a comprehensive understanding of embodiments. Thus, it is apparent that embodiments can be carried out without those specifically defined matters. Also, well-known functions or constructions are not described in detail since they would obscure embodiments with unnecessary detail.

The present specification does not describe all components in the embodiments, and common knowledge in the art or the same descriptions of the embodiments will be omitted below. The term "part" or "portion" used herein may be implemented using hardware or software, and according to embodiments, a plurality of "parts" or "portions" may be formed as a single unit or element, or one "part" or "portion" may include a plurality of units or elements. Expressions such as "at least one of," when preceding a list of elements, modify the entire list of elements and do not modify the individual elements of the list. Hereinafter, the operating principles and embodiments of the disclosure will be described in detail with reference to the accompanying drawings.

In embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be a cart-type or a portable-type ultrasound diagnosis apparatus, which is portable, moveable, mobile, or hand-held. Examples of the portable-type ultrasound diagnosis apparatus may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an embodiment is not limited thereto.

An example of the ultrasound diagnosis apparatus 100 according to the present embodiment is described below with reference to FIGS. 2A, 2B, and 2C.

FIGS. 2A, 2B, and 2C are diagrams illustrating ultrasound diagnosis apparatuses 100a, 100b, and 100c according to an embodiment.

Referring to FIGS. 2A and 2B, the ultrasound diagnosis apparatus (100a, 100b) may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus (100a, 100b). The main display 121 and the sub-display 122 may provide graphical user interfaces (GUI), thereby receiving user's inputs of data to control the ultrasound diagnosis apparatus (100a. 100b). For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus (100a. 100b) may control the display of the ultrasound image on the main display 121 by using the input control data.

Referring to FIG. 2B, the ultrasound diagnosis apparatus 100b may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100b may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100c may be implemented as portable ultrasound diagnosis apparatus. An example of the portable ultrasound diagnosis apparatus may include, for example, smart phones including probes and applications, laptop computers, personal digital assistants (PDAs), or tablet PCs, but an embodiment is not limited thereto.

The ultrasound diagnosis apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100c, and a GUI.

Figure 3:
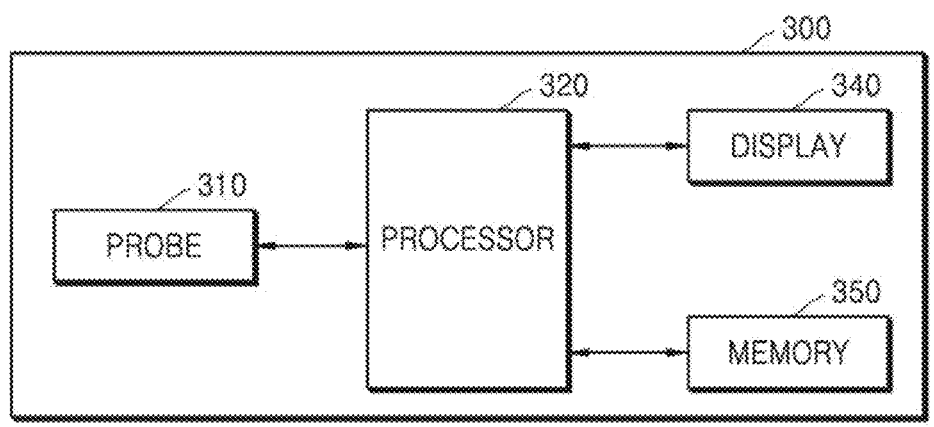
FIG. 3 is a block diagram of a configuration of an ultrasound diagnosis apparatus according to an embodiment.

FIG. 3 is a block diagram of a configuration of an ultrasound diagnosis apparatus 300 according to an embodiment.

According to an embodiment, the ultrasound diagnosis apparatus 300 may include any image processing apparatus capable of obtaining an ultrasound image based on ultrasound image data acquired by performing ultrasound scanning. Furthermore, the ultrasound diagnosis apparatus 300 may include a computing device capable of controlling acquisition of ultrasound image data during an ultrasound scan.

The ultrasound diagnosis apparatus 300 may be an apparatus having a function of receiving ultrasound image data acquired by performing ultrasound scanning, processing the ultrasound image data, and displaying a result. In an embodiment, the ultrasound diagnosis apparatus 300 may include a medical server device installed in a hospital where a patient has an ultrasound scan or other medical care facilities. The ultrasound diagnosis apparatus 300 is not limited thereto and may include a smartphone, a tablet PC, a PC, a smart TV, a mobile phone, a personal digital assistant (PDA), a laptop, a media player, a digital camera, a home appliance, and other mobile or non-mobile computing devices.

Referring to FIG. 3, the ultrasound diagnosis apparatus 300 may include a probe 310, a processor 320, a display 340, and a memory 350.

The ultrasound diagnosis apparatus 300 may be included in the ultrasound diagnosis apparatus 100 described with reference to FIG. 1. In this case, the probe 310, the display 340, and the memory 350 of the ultrasound diagnosis apparatus 300 may respectively correspond to the probe 20, the display 140, and the storage 150 of the ultrasound diagnosis apparatus 100 of FIG. 1. Furthermore, the processor 320 may correspond to one or a combination of the controller 120 and the image processor 130 described with reference to FIG. 1.

The components of the ultrasound diagnosis apparatus 300 are not limited to those shown in FIG. 3. According to an embodiment, the ultrasound diagnosis apparatus 300 may include more components than those shown in FIG. 3, or may not include some of the components shown in FIG. 3.

In an embodiment, the ultrasound diagnosis apparatus 300 may further include a communicator (not shown) including one or more components that enable communication with at least one of a client device, an external server, and an external database.

The probe 310 may acquire 3D volume data with respect to an object. In an embodiment, the probe 310 may transmit an ultrasound signal to the object and receive an echo signal reflected from the object. The probe 310 may also process the received echo signal to thereby generate 3D ultrasound volume data with respect to the object.

The probe 310 may be formed integrally with the ultrasound diagnosis apparatus 300 or be separated from the ultrasound diagnosis apparatus 300 and connected thereto by wire or wirelessly. Examples of the probe 310 may include a 2D or 3D mechanical probe, a 2D array probe, etc.

The ultrasound diagnosis apparatus 300 may acquire 3D ultrasound volume data via the probe 310 or receive 3D volume data generated by an external ultrasound diagnosis apparatus, MRI apparatus, CT apparatus, etc. instead of directly producing the same.

According to an embodiment, the processor 320 may control all operations of the probe 310, the display 340, and the memory 350. The processor 320 may control all operations of the ultrasound diagnosis apparatus 300 by executing a program stored in the memory 350. Furthermore, the processor 320 may include one or more processors.

According to an embodiment, the processor 320 may obtain an ultrasound image of the object based on the ultrasound image data with respect to the object. For example, the processor 320 may obtain an ultrasound image by processing the acquired ultrasound volume data in real-time. The ultrasound image obtained in real-time by the processor 320 may be a still image or moving image. The processor 320 may obtain an ultrasound image based on ultrasound volume data received via an external device or by scanning the object via the probe 310.

Furthermore, the processor 320 may control the display 340 to display an ultrasound image generated in real-time.

The processor 320 may identify a plurality of 2D cross-sections, each including at least one feature to be observed, based on 3D ultrasound volume data.

The plurality of 2D cross-sections may be identified by searching cross-sections respectively perpendicular to an x-axis, a y-axis, and a z-axis and corresponding to 3D ultrasound volume data with respect to an ROI. Furthermore, the plurality of 2D cross-sections may be identified by searching cross-sections respectively parallel to x-, y-, and z-axes and corresponding to 3D ultrasound volume data with respect to an ROI.

The processor 320 may determine priority levels of the identified 2D cross-sections based on at least one feature included in each of the 2D cross-sections. A priority level may be determined based on a degree of inclusion of a feature to be observed in a 2D cross-section. In an embodiment, the processor 320 may acquire an area and a number of portions including at least one feature in each of the 2D cross-sections and determine priority levels of the 2D cross-sections based on the acquired area and number of portions.

The processor 320 may display a plurality of 2D ultrasound images respectively corresponding to at least some of the 2D cross-sections based on the priority levels.

According to an embodiment, the processor 320 may display a plurality of 2D ultrasound images in an order that at least one feature is well represented in the plurality of 2D ultrasound images.

The at least one feature to be observed may include at least one of a particular shape, a texture, a propensity, and a characteristic portion of a tissue in an ROI.

According to an embodiment, the display 340 may display, according to control by the processor 320, an ultrasound image generated based on acquired ultrasound image data and information related to the ultrasound image.

According to an embodiment, the ultrasound diagnosis apparatus 300 may automatically identify cross-sections, each including the at least one feature to be observed, and display the identified cross-sections according to their priority levels. This configuration may facilitate diagnosis of the object based on the displayed cross-sections, each including at least one feature to be observed.

Figure 4:
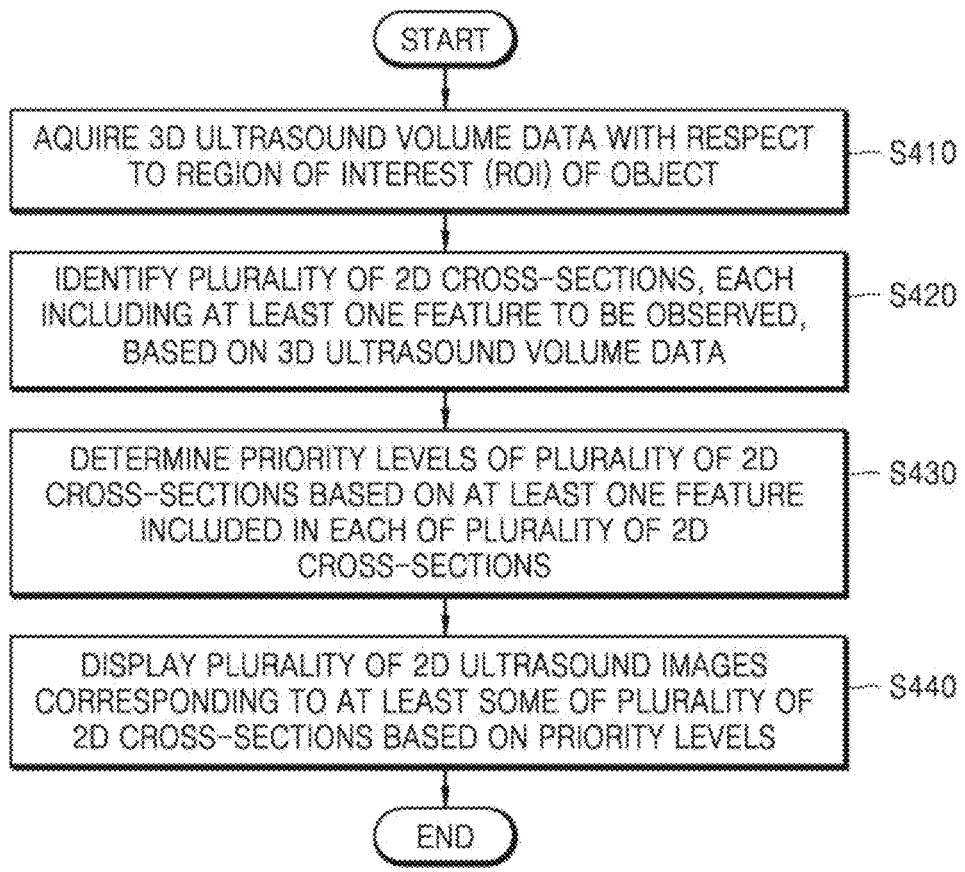
FIG. 4 is flowchart of a method of controlling an ultrasound diagnosis apparatus, according to an embodiment.

FIG. 4 is flowchart of a method of controlling an ultrasound diagnosis apparatus, according to an embodiment.

In an embodiment, the method of FIG. 4 may be performed by the ultrasound diagnosis apparatus 300 described with reference to FIG. 3.

The ultrasound diagnosis apparatus 300 may acquire 3D ultrasound volume data with respect to an ROI of an object (S410).

The ultrasound diagnosis apparatus 300 may identify a plurality of 2D cross-sections, each including at least one feature to be observed, based on the 3D ultrasound volume data (S420).

The ultrasound diagnosis apparatus 300 may determine priority levels of the plurality of 2D cross-sections based on at least one feature included in each of the plurality of 2D cross-sections (S430).

A priority level may be determined based on a degree of inclusion of the at least one feature in each of the plurality of 2D cross-sections. A priority level may become higher as the number and area of portions including the at least one feature in each of the plurality of 2D cross-sections increase.

The ultrasound diagnosis apparatus 300 may display a plurality of 2D ultrasound images respectively corresponding to at least some of the plurality of 2D cross-sections based on the determined priority levels (S440).

The plurality of 2D ultrasound images may correspond to a predetermined number of 2D cross-sections ranked in a descending priority order among the plurality of 2D cross-sections.

Figure 5:
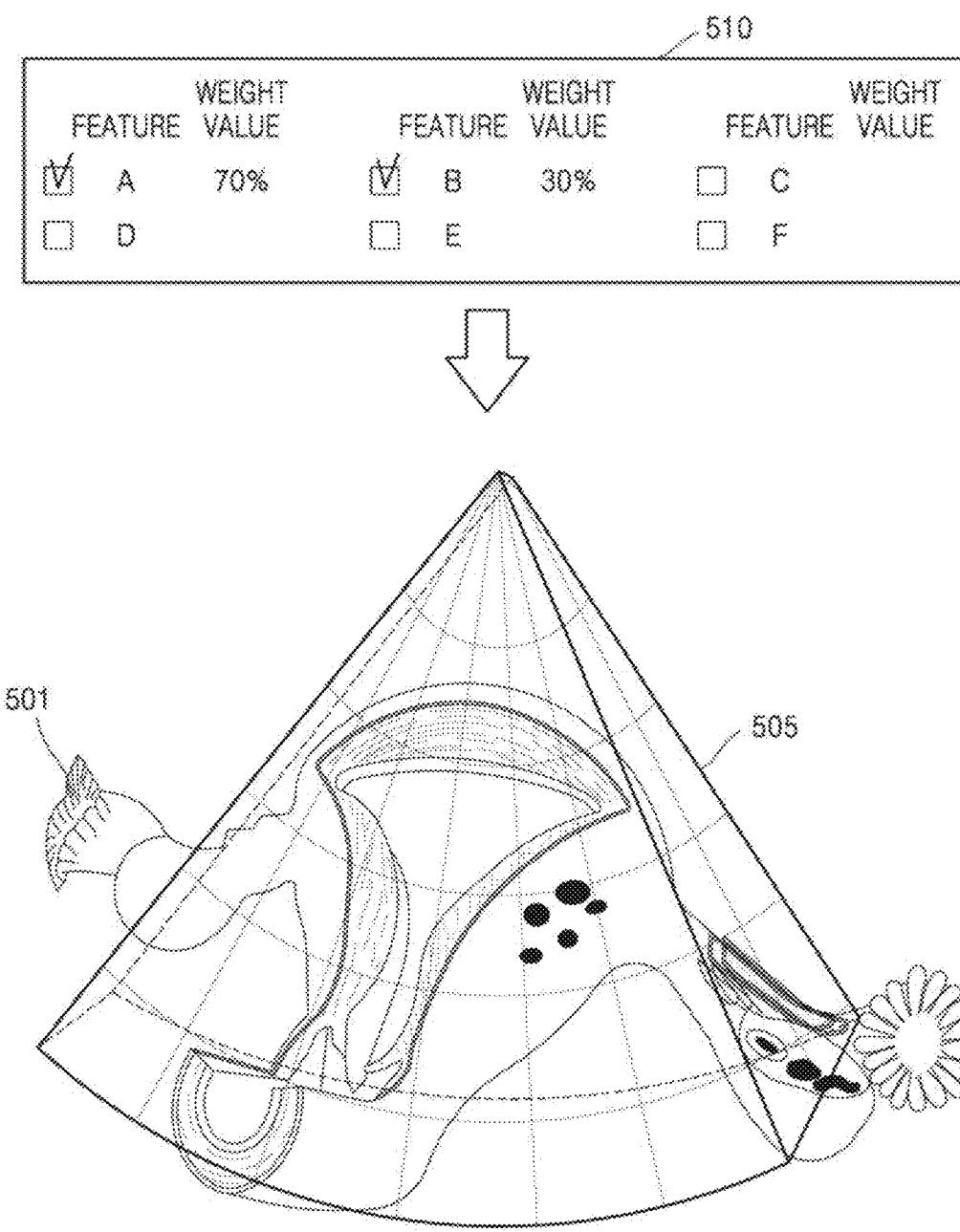
FIG. 5 illustrates an example in which an ultrasound diagnosis apparatus receives at least one feature to be observed.

FIG. 5 illustrates an example in which the ultrasound diagnosis apparatus 300 receives at least one feature to be observed.

The ultrasound diagnosis apparatus 300 may determine at least one feature to be observed based on a user input. For example, the ultrasound diagnosis apparatus 300 may receive a feature to be observed via a user interface 510. A feature to be observed may be a feature that is to be included in a 2D ultrasound image via the ultrasound diagnosis apparatus 300.

As shown in FIG. 5, the ultrasound diagnosis apparatus 300 may receive a plurality of features from a user via the user interface 510. In this case, the ultrasound diagnosis apparatus 300 may additionally acquire an input for a weight value via the user interface 510.

When the user does not select a weight value, the ultrasound diagnosis apparatus 300 may determine a predetermined value as being the weight value. For example, when the user does not select a weight value, the ultrasound diagnosis apparatus 300 may determine an equal weight for a plurality of features.

After determining the at least one feature to be observed, the ultrasound diagnosis apparatus 300 may acquire 3D volume data 505 with respect to an ROI of an object 501. Furthermore, the ultrasound diagnosis apparatus 300 may acquire the 3D volume data 505 with respect to the ROI of the object 501 before determining the at least one feature to be observed.

In an embodiment, the ultrasound diagnosis apparatus 300 may acquire the 3D volume data 505 with respect to the ROI by using a 2D or 3D mechanical probe or a 2D array probe. Furthermore, the ultrasound diagnosis apparatus 300 may obtain a panoramic image by using a 2D or 3D mechanical probe or 2D array probe. The ultrasound diagnosis apparatus 300 may use a sensor to find a cross-section including at least one feature to be observed.

Figure 6A:
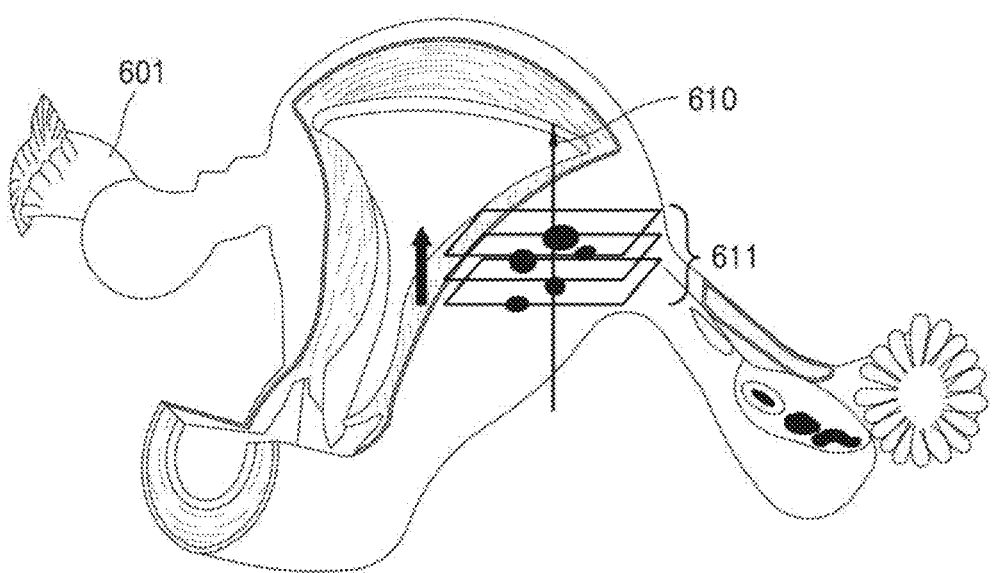
FIGS. 6A through 6C are diagrams for explaining an example in which an ultrasound diagnosis apparatus searches 2D cross-sections based on volume data with respect to a region of interest (ROI) of an object, according to an embodiment.
Figure 6B:
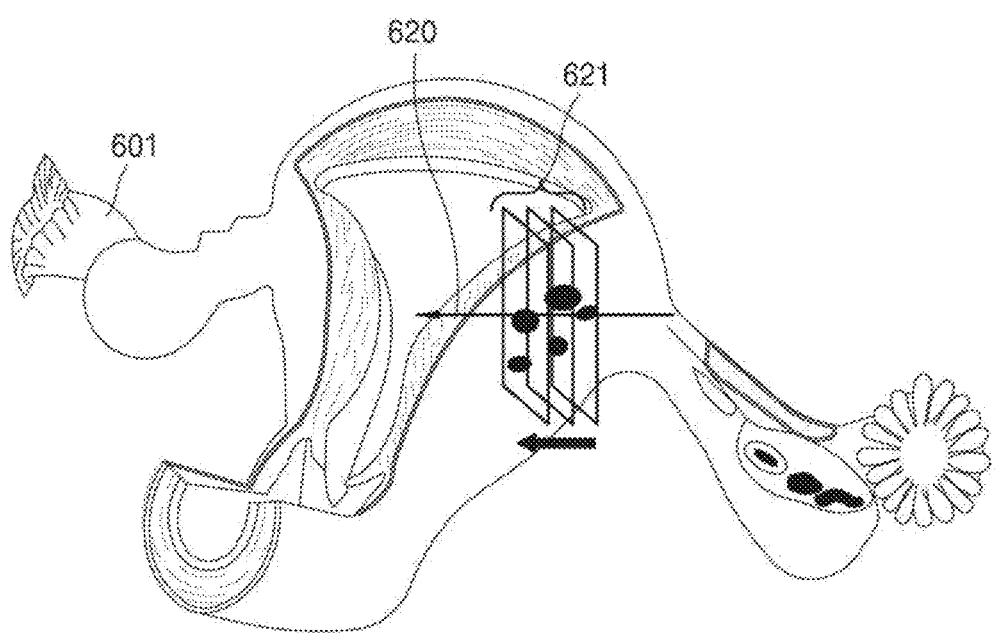
Figure 6C:
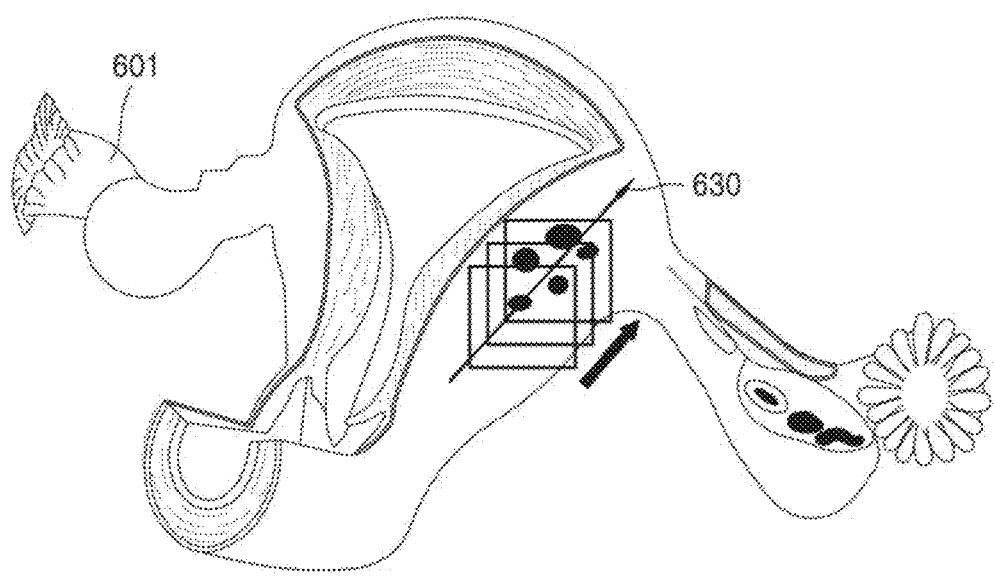

FIGS. 6A through 6C are diagrams for explaining an example in which the ultrasound diagnosis apparatus 300 searches 2D cross-sections based on volume data regarding an ROI of an object, according to an embodiment.

The ultrasound diagnosis apparatus 300 may search cross-sections respectively perpendicular to a first axis, a second axis, and a third axis with respect to 3D ultrasound volume data regarding an ROI to thereby acquire a plurality of 2D cross-sections, each including a feature to be observed.

Referring to FIG. 6A, the ultrasound diagnosis apparatus 300 searches cross-sections 611 perpendicular to a first axis 610 with respect to 3D ultrasound volume data regarding an ROI of an object 601.

Referring to FIG. 6B, the ultrasound diagnosis apparatus 300 searches cross-sections 621 perpendicular to a second axis 620 with respect to the 3D ultrasound volume data regarding the ROI of the object 601. The second axis 620 may be orthogonal to the first axis 610. The first and second axes 610 and 620 may correspond to the x- and y-axes, respectively.

Referring to FIG. 6C, the ultrasound diagnosis apparatus 300 searches cross-sections 631 perpendicular to a third axis 630 with respect to the 3D ultrasound volume data regarding the ROI of the object 601. The third axis 630 may be simultaneously orthogonal to the first and second axes 610 and 620. The first, second, and third axes 610, 620, and 630 may correspond to the x-, y-, and z-axes, respectively.

Figure 7A:
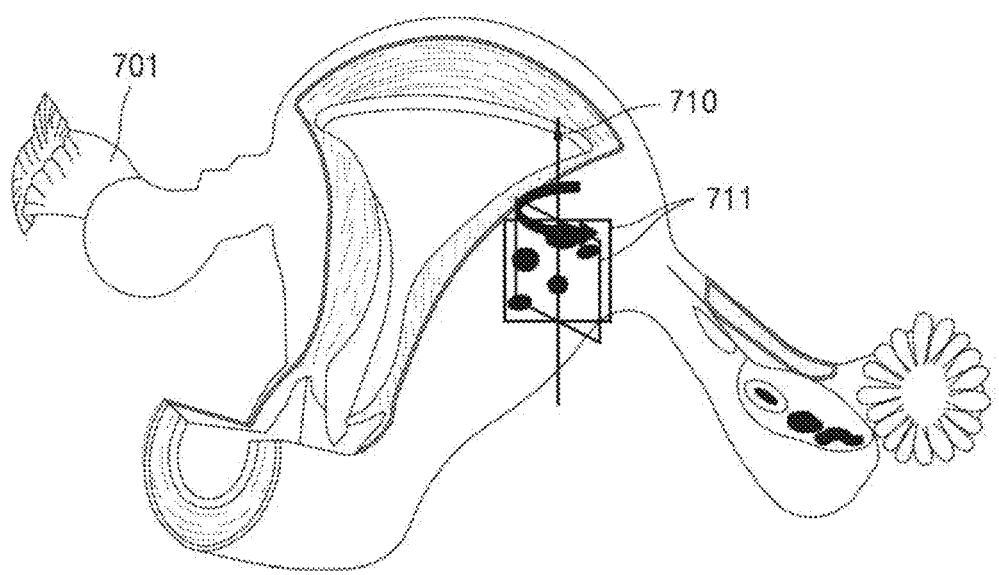
FIGS. 7A through 7C are diagrams for explaining another example in which an ultrasound diagnosis apparatus searches 2D cross-sections based on volume data with respect to an ROI of an object, according to an embodiment.
Figure 7B:
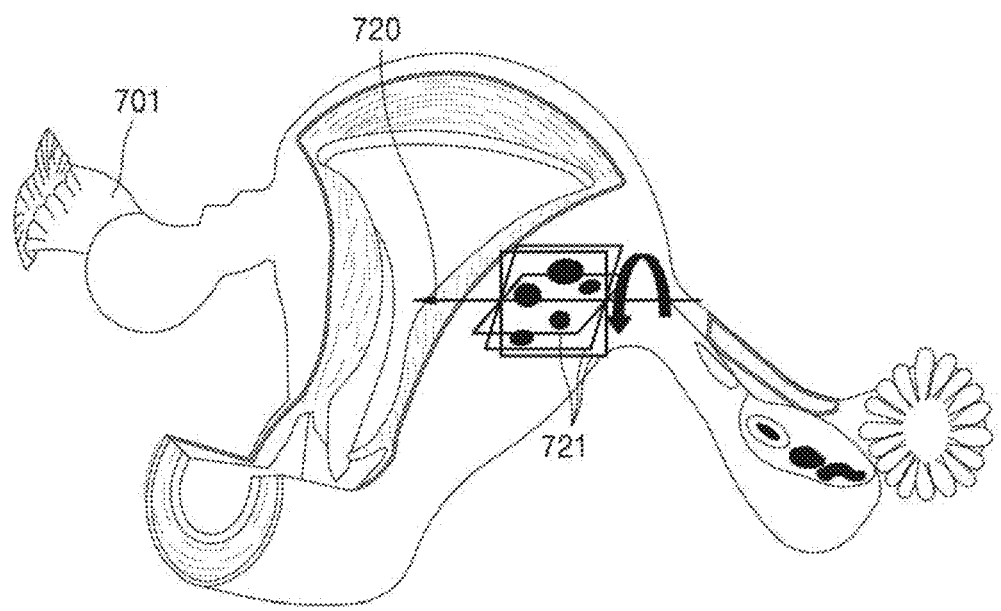
Figure 7C:
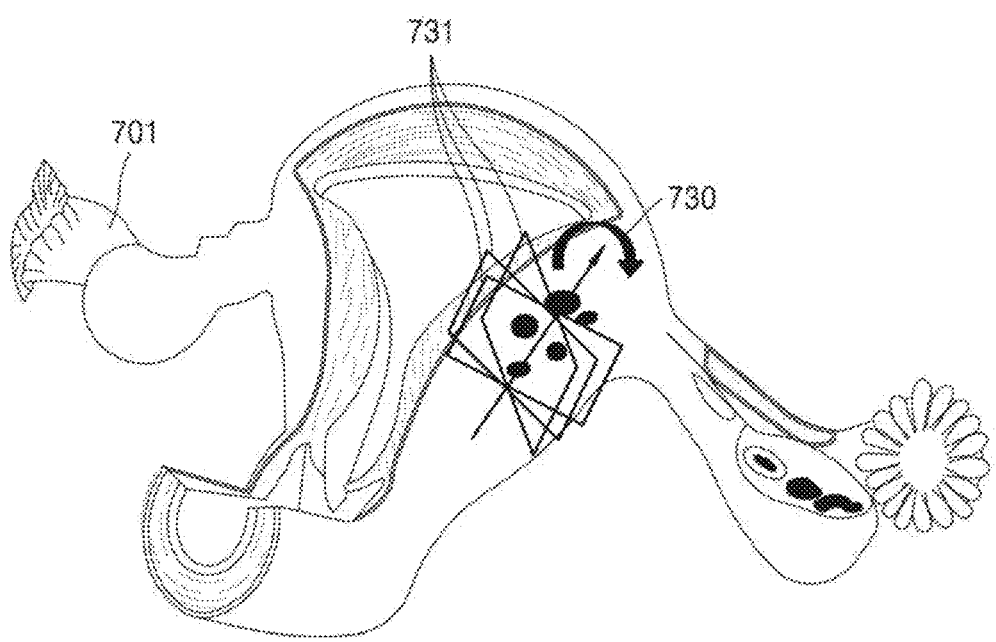

FIGS. 7A through 7C are diagrams for explaining another example in which the ultrasound diagnosis apparatus 300 searches 2D cross-sections based on volume data regarding an ROI of an object, according to an embodiment.

The ultrasound diagnosis apparatus 300 may search cross-sections respectively parallel to a first axis, a second axis, and a third axis with respect to 3D ultrasound volume data regarding an ROI to thereby acquire a plurality of 2D cross-sections, each including a feature to be observed.

Referring to FIG. 7A, the ultrasound diagnosis apparatus 300 searches cross-sections 711 parallel to a first axis 710 with respect to 3D ultrasound volume data regarding an ROI of an object 701.

Referring to FIG. 7B, the ultrasound diagnosis apparatus 300 searches cross-sections 721 parallel to a second axis 720 with respect to the 3D ultrasound volume data regarding the ROI of the object 701. The second axis 720 may be orthogonal to the first axis 710. The first and second axes 710 and 720 may correspond to the x- and y-axes, respectively.

Referring to FIG. 7C, the ultrasound diagnosis apparatus 300 searches cross-sections 731 parallel to a third axis 730 with respect to the 3D ultrasound volume data regarding the ROI of the object 701. The third axis 730 may be orthogonal to both the first and second axes 710 and 720. The first, second, and third axes 710, 720, and 730 may correspond to the x-, y-, and z-axes, respectively.

FIG. 8 is a diagram for explaining an example in which the ultrasound diagnosis apparatus 300 determines priority levels of a plurality of 2D cross-sections based on at least one feature included in each 2D cross-section, according to an embodiment.

The ultrasound diagnosis apparatus 300 may identify a plurality of 2D cross-sections 810, each including at least one feature to be observed, based on 3D ultrasound volume data regarding an ROI of an object 801.

The ultrasound diagnosis apparatus 300 may acquire an area and the number of portions including at least one feature in each of the plurality of 2D cross-sections 810 and determine priority levels of the 2D cross-sections 810 based on at least one of the area and number.

In an embodiment, when at least one feature to be observed includes features A and B, the ultrasound diagnosis apparatus 300 may identify the 2D cross-sections 810, each including at least one of the feature A and feature B.

In an embodiment, the identified 2D cross-sections 810 may include first through fourth cross-sections 811, 813, 815, and 817, and the ultrasound diagnosis apparatus 300 may acquire an area and a number of at least one of the feature A and feature B included in each of the identified 2D cross-sections 810.

In an embodiment, the ultrasound diagnosis apparatus 300 may determine the priority levels of the 2D cross-sections 810 in a decreasing order of a sum of the numbers of the feature A and feature B included in each of the 2D cross-sections 810, i.e., in an order from the largest to the smallest. The sum of the numbers of feature A and feature B may be a weighted sum obtained by respectively multiplying the numbers of feature A and feature B by their corresponding weight values and adding resulting values.

In another embodiment, the ultrasound diagnosis apparatus 300 may determine the priority levels of the 2D cross-sections 810 in a decreasing order of a sum of areas of feature A and feature B included in each of the 2D cross-sections 810, i.e., in the order from the largest to the smallest. The sum of the areas of feature A and feature B may be a weighted sum obtained by respectively multiplying the areas of feature A and feature B by their corresponding weight values and adding resulting values.

According to an embodiment, at least one feature to be observed may include at least one of a particular shape, a texture, a propensity, and a characteristic portion of a tissue in an ROI.

In an embodiment, a particular shape of a tissue may include an oval shape, a round shape, an echo shape with even or uneven boundaries, or an echo shape having a needle or v shape.

A texture of a tissue may include at least one of a rough portion, an uneven portion, a portion having a comb-like pattern, a spot, and a shaded portion within the tissue.

A propensity of a tissue may include at least one of tissue hardness, the degree of attenuation of ultrasound waves, and a position and an area where a specific color is distributed.

A characteristic portion of a tissue may include at least one of a cystic portion, a calcified portion, an injured portion, a ruptured portion, and an anechoic portion. According to an embodiment, different weight values may be applied to a feature according to the degrees of cyst development, calcification, injury, and rupture.

At least one feature to be observed may be determined according to predetermined conditions. In an embodiment, the predetermined conditions may be a feature having a size larger than or equal to a specific size within a tissue and a feature having a thickness larger than or equal to a specific thickness.

The ultrasound diagnosis apparatus 300 may search for at least one feature to be observed by using a computer aided diagnosis (CAD) system. Furthermore, the ultrasound diagnosis apparatus 300 may search for at least one feature to be observed by using at least one of machine learning and deep learning methods.

FIGS. 9A and 9B are diagrams for explaining an example in which the ultrasound diagnosis apparatus 300 displays a plurality of 2D ultrasound images respectively corresponding to at least some of a plurality of 2D cross-sections based on their priority levels, according to an embodiment.

Referring to FIGS. 9A and 9B, the ultrasound diagnosis apparatus 300 may display a plurality of 2D ultrasound images 900 corresponding to at least some of a plurality of 2D cross-sections based on a priority level.

The ultrasound diagnosis apparatus 300 may display the plurality of 2D ultrasound images 900 corresponding to a predetermined number of 2D cross-sections ranked in a descending priority order among a plurality of 2D cross-sections of which priority levels are determined. For example, the 2D ultrasound images 900 may include first through fourth images 910, 920, 930, and 940. Furthermore, the ultrasound diagnosis apparatus 300 may display the 2D ultrasound images 900 together with a 3D image obtained based on ultrasound volume data. In this case, the 3D image may be any type of image that represents a shape of an object three-dimensionally. In detail, the 3D image may include a 3D ultrasound image rendered based on ultrasound volume data regarding the object. Furthermore, the 3D image may include an image that roughly represents the object based on ultrasound volume data regarding the object.

Furthermore, the ultrasound diagnosis apparatus 300 may display the 2D ultrasound images 900 in an order that at least one feature to be observed is well represented therein.

In addition, the ultrasound diagnosis apparatus 300 may provide the 2D ultrasound images 900 according to modes such as a brightness (B) mode, a Doppler mode, an elastic mode, etc., such that at least one feature to be observed is well represented therein.

Referring to FIG. 9A, the ultrasound diagnosis apparatus 300 may change the order in which the 2D ultrasound images 900 are displayed, based on a user input for changing priority levels of the 2D ultrasound images 900 to be displayed.

Furthermore, referring to FIG. 9B, when the 2D ultrasound images 900 include an image that does not represent a feature to be observed properly, the ultrasound diagnosis apparatus 300 may not display the image among the 2D ultrasound images 900 to be displayed based on a user input.

FIGS. 10A through 10E are diagrams for explaining an example in which the ultrasound diagnosis apparatus 300 displays a 2D ultrasound image in real-time while identifying a cross-section including at least one feature to be observed, according to an embodiment.

While identifying a plurality of 2D cross-sections, each including at least one feature to be observed, the ultrasound diagnosis apparatus 300 may update in real-time priority levels of the plurality of 2D cross-sections and a plurality of 2D ultrasound images corresponding to the plurality of 2D cross-sections based on at least one feature included in each of the plurality of 2D cross-sections.

The ultrasound diagnosis apparatus 300 may also display a plurality of 2D ultrasound images respectively corresponding to at least some of the plurality of 2D cross-sections based on the updated priority levels.

FIG. 10A illustrates an order in which the ultrasound diagnosis apparatus 300 identifies 2D cross-sections, each including at least one feature to be observed.

The ultrasound diagnosis apparatus 300 may identify the 2D cross-sections, each including at least one feature to be observed, by scanning an object 1001. In an embodiment, the ultrasound diagnosis apparatus 300 may identify the 2D cross-sections, each including the at least one feature to be observed, in a sequential order, from a first cross-section 1011 to a fourth cross-section 1017.

FIGS. 10B through 10E illustrate an order in which the ultrasound diagnosis apparatus 300 displays 2D ultrasound images when respectively identifying the 2D cross-sections in a sequential order from the first cross-section 1011 to the fourth cross-section 1017.

Figure 10B:
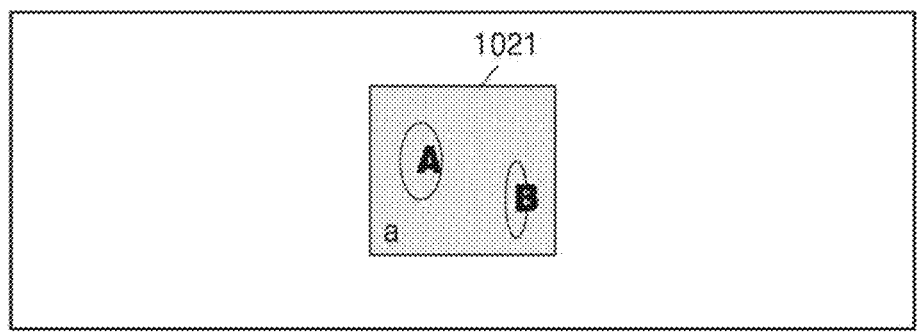

Referring to FIG. 10B, the ultrasound diagnosis apparatus 300 may first identify the first cross-section 1011 including at least one feature to be observed.

The ultrasound diagnosis apparatus 300 may determine a priority level of the first cross-section 1011 as a first priority level and display image a 1021 corresponding to the first cross-section 1011.

Figure 10C:
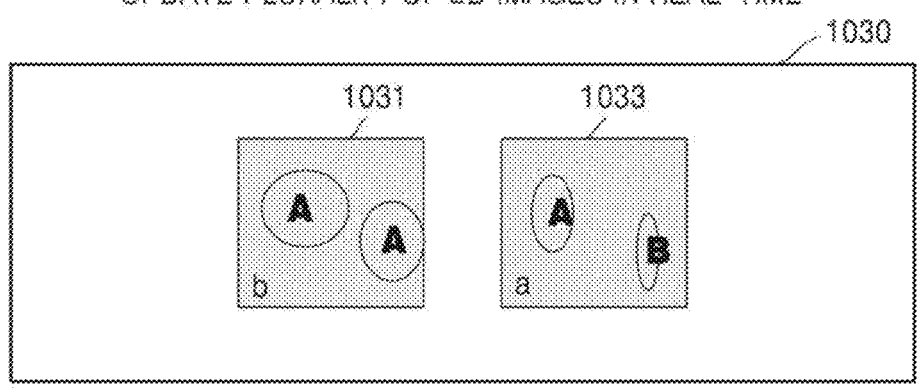

Referring to FIG. 10C, the ultrasound diagnosis apparatus 300 may further identify a second cross-section 1013 including at least one feature to be observed.

A priority level of image b 1031 corresponding to the further identified second cross-section 1013 may be updated to a first priority level while a priority level of image a 1033 may be updated to a second priority level. The ultrasound diagnosis apparatus 300 may display a plurality of 2D ultrasound images 1030 in an order from image b 1031 to image a 1033.

Figure 10D:
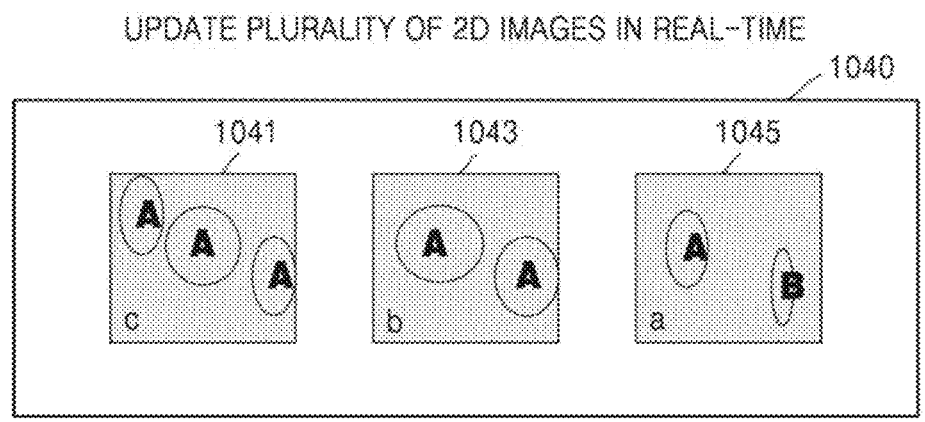

Referring to FIG. 10D, the ultrasound diagnosis apparatus 300 may further identify a third cross-section 1015 including at least one feature to be observed.

A priority level of image c 1041 corresponding to the further identified third cross-section 1015 may be updated to a first priority level while priority levels of image b 1043 and image a 1045 may be respectively updated to second and third priority levels. The ultrasound diagnosis apparatus 300 may display a plurality of 2D ultrasound images 1040 in an order from image c 1041 to image b 1043 to image a 1045.

Figure 10E:
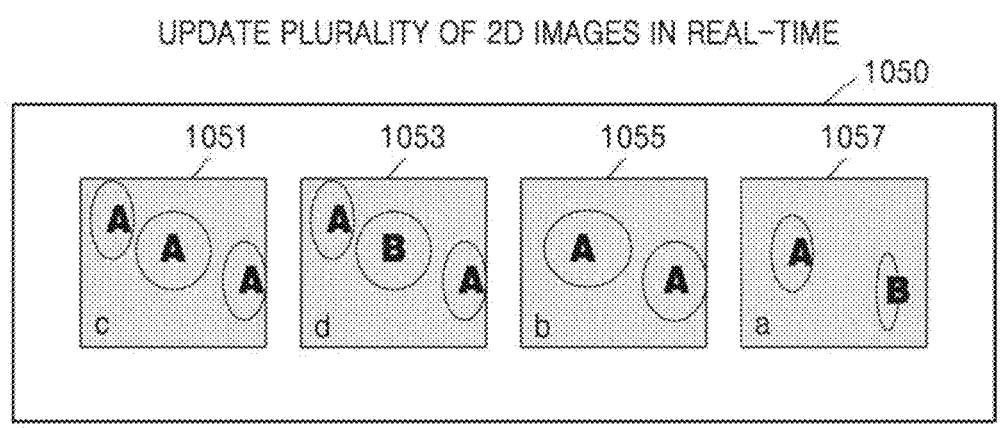

Referring to FIG. 10E, the ultrasound diagnosis apparatus 300 may further identify the fourth cross-section 1017 including at least one feature to be observed.

A priority level of image c 1051 corresponding to the third cross-section 1015 may be kept at a first priority level while priority levels of image d 1053 corresponding to the fourth cross-section 1017, image b 1055, and image a 1057 may be respectively updated to second through fourth priority levels. The ultrasound diagnosis apparatus 300 may display a plurality of 2D ultrasound images 1050 in an order from image c 1051 to imaged 1053 to image b 1055 to image a 1057.

According to an embodiment, the ultrasound diagnosis apparatus 300 may determine a priority level of a cross-section identified in real-time based on at least one feature included in the real-time identified cross-section and at least one feature in each of at least one previously identified cross-section.

The ultrasound diagnosis apparatus 300 may display, based on determined priority levels, a plurality of 2D ultrasound images respectively corresponding to at least some of the real-time identified cross-section and the at least one previously identified cross-section.

FIG. 11 is a flowchart of a method of controlling the ultrasound diagnosis apparatus 300, according to an embodiment.

For example, the method of FIG. 11 may be performed by the ultrasound diagnosis apparatus 300.

The ultrasound diagnosis apparatus 300 may acquire 3D ultrasound volume data with respect to an ROI of an object (S1110).

The ultrasound diagnosis apparatus 300 may identify a plurality of 2D cross-sections, each including at least one feature to be observed, based on the 3D ultrasound volume data (S1120).

The ultrasound diagnosis apparatus 300 may determine priority levels of the plurality of 2D cross-sections based on at least one feature included in each of the 2D cross-sections (S1130).

The ultrasound diagnosis apparatus 300 may display a plurality of 2D ultrasound images respectively corresponding to at least some of the plurality of 2D cross-sections based on the determined priority levels (S1140).

The ultrasound diagnosis apparatus 300 may display a result of diagnosis based on the at least one feature included in each of the 2D cross-sections (S1150).

Figure 12:
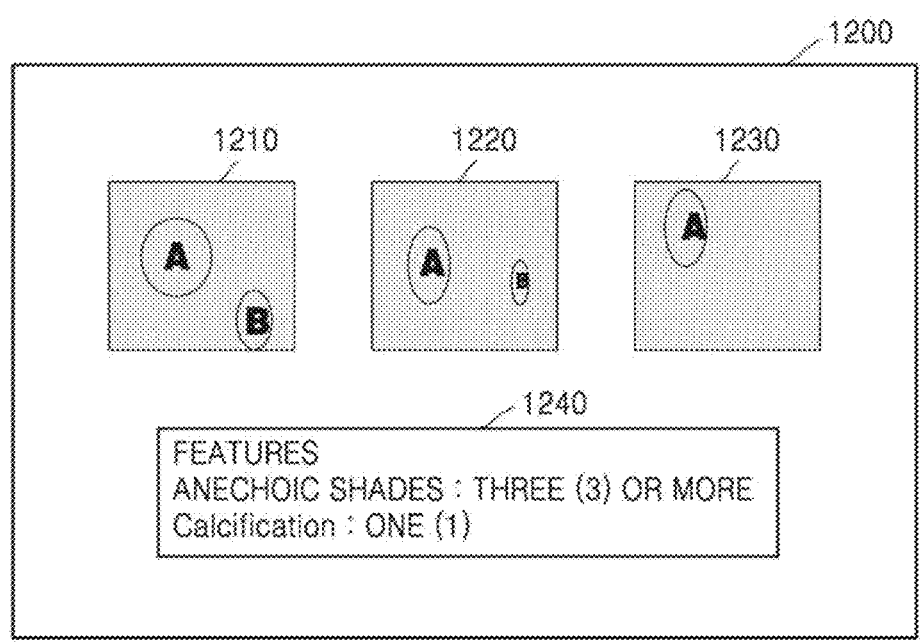
FIG. 12 illustrates an example in which an ultrasound diagnosis apparatus displays a screen showing a result of diagnosis based on at least one feature included in each of a plurality of 2D cross-sections, according to an embodiment.

FIG. 12 illustrates an example in which the ultrasound diagnosis apparatus 300 displays a screen showing a result of diagnosis based on at least one feature included in each of a plurality of 2D cross-sections, according to an embodiment.

The ultrasound diagnosis apparatus 300 may display a result 1240 of integrating found features included in first through third images 1210, 1220, and 1230. The ultrasound diagnosis apparatus 300 may display the first through third images 1210, 1220, and 1230 together with a 3D image generated based on acquired ultrasound volume data. In this case, the 3D image may be any type of image that represents a shape of an object three-dimensionally. The 3D image may include a 3D ultrasound image rendered based on ultrasound volume data regarding the object and an image that roughly represents the object based on the ultrasound volume data regarding the object.

When the ultrasound diagnosis apparatus 300 displays a 3D ultrasound image together with the first through third images 1210, 1220, and 1230, cross-sections respectively depicted in the first through third images 1210, 1220 and 1230 may be displayed in the 3D ultrasound image. Furthermore, the ultrasound diagnosis apparatus 300 may display, together with the first through third images 1210, 1220, and 1230, a 3D image in which portions corresponding to found features included in the first through third images 1210, 1220, and 1230 are emphasized in such a manner as to well represent the features.

Furthermore, the ultrasound diagnosis apparatus 300 may combine the found features to diagnose a suspected disease and display the suspected disease together. In an embodiment, the ultrasound diagnosis apparatus 300 may diagnose suspected diseases by using a computer aided diagnosis (CAD) system. In addition, the ultrasound diagnosis apparatus 300 may diagnose suspected diseases by using at least one of machine learning and deep learning techniques.

Embodiments may be implemented through non-transitory computer-readable recording media having recorded thereon computer-executable instructions and data. The instructions may be stored in the form of program codes, and when executed by a processor, generate a predetermined program module to perform a specific operation. Furthermore, when being executed by the processor, the instructions may perform specific operations according to the embodiments.

What is claimed is:

1. An ultrasound diagnosis apparatus comprising:
a display;
a memory storing one or more instructions; and
at least one processor configured to execute the stored one or more instructions to:
acquire three-dimensional (3D) ultrasound volume data regarding a region of interest of an object;
identify a plurality of two-dimensional (2D) cross-sections, each including at least one feature to be observed, based on the 3D ultrasound volume data;
determine priority levels of the plurality of 2D cross-sections based on the at least one feature included in each of the plurality of 2D cross-sections; and
control the display to display a plurality of 2D ultrasound images respectively corresponding to at least some of the plurality of 2D cross-sections based on the priority levels,
wherein the at least one feature to be observed comprises at least one of a shape, a texture, a propensity, and a characteristic portion of a tissue in the region of interest.

2. The ultrasound diagnosis apparatus of claim 1, wherein the at least one processor is further configured to execute the stored one or more instructions to control the display to display the plurality of 2D ultrasound images in a descending order of the priority levels.

3. The ultrasound diagnosis apparatus of claim 1, wherein the at least one processor is further configured to execute the stored one or more instructions to change, based on a user input, an order in which the plurality of 2D ultrasound images are displayed.

4. The ultrasound diagnosis apparatus of claim 1, wherein the at least one processor is further configured to execute the stored one or more instructions to determine, based on a user input, an ultrasound image that is not to be displayed from among the plurality of 2D ultrasound images.

5. The ultrasound diagnosis apparatus of claim 1, wherein the plurality of 2D cross-sections are acquired by searching cross-sections respectively perpendicular to a first axis, a second axis, and a third axis with respect to the 3D ultrasound volume data regarding the region of interest, and wherein the first through third axes are orthogonal to one another.

6. The ultrasound diagnosis apparatus of claim 1, wherein the plurality of 2D cross-sections are acquired by searching cross-sections respectively parallel to a first axis, a second axis, and a third axis with respect to the 3D ultrasound volume data regarding the region of interest, and
wherein the first through third axes are orthogonal to one another.

7. The ultrasound diagnosis apparatus of claim 1, wherein the determining of the priority levels of the plurality of 2D cross-sections comprises acquiring an area and a number of portions including the at least one feature in each of the plurality of 2D cross-sections and determining the priority levels of the plurality of 2D cross-sections based on at least one of the area and the number.

8. The ultrasound diagnosis apparatus of claim 1, wherein the at least one processor is further configured to execute the stored one or more instructions to determine at least one feature to be observed based on a user input.

9. The ultrasound diagnosis apparatus of claim 1, wherein the at least one feature to be observed comprises a plurality of features respectively having predetermined weight values, and
wherein the at least one processor is further configured to execute the stored one or more instructions to determine the priority levels of the plurality of 2D cross-sections based on the plurality of features to which the predetermined weight values are respectively applied.

10. The ultrasound diagnosis apparatus of claim 1, wherein the at least one processor is further configured to execute the stored one or more instructions to:
update the priority levels of the plurality of 2D cross-sections based on the at least one feature while respectively identifying the plurality of 2D cross-sections; and
control the display to display the plurality of 2D ultrasound images respectively corresponding to at least some of the plurality of 2D cross-sections based on the updated priority levels.

11. The ultrasound diagnosis apparatus of claim 1, wherein the at least one processor is further configured to execute the stored one or more instructions to control the display to display a result of diagnosis based on the at least one feature included in each of the plurality of 2D cross-sections.

12. The ultrasound diagnosis apparatus of claim 1, wherein the at least one processor is further configured to execute the stored one or more instructions to:
control the display to display a 3D ultrasound image obtained based on the 3D ultrasound volume data, together with the plurality of 2D ultrasound images; and
control the display to display cross-sections corresponding to the plurality of 2D ultrasound images in the 3D image.

13. A method of controlling an ultrasound diagnosis apparatus, the method comprising:
acquiring three-dimensional (3D) ultrasound volume data regarding a region of interest of an object;
identifying a plurality of two-dimensional (2D) cross-sections, each including at least one feature to be observed, based on the 3D ultrasound volume data;
determining priority levels of the plurality of 2D cross-sections based on the at least one feature included in each of the plurality of 2D cross-sections; and displaying a plurality of 2D ultrasound images respectively corresponding to at least some of the plurality of 2D cross-sections based on the priority levels,
wherein the at least one feature to be observed comprises at least one of a shape, a texture, a propensity, and a characteristic portion of a tissue in the region of interest.

14. The method of claim 13, wherein the displaying of the plurality of 2D ultrasound images comprises displaying the plurality of 2D ultrasound images in a descending order of the priority levels.

15. The method of claim 13, wherein the displaying of the plurality of 2D ultrasound images comprises changing, based on a user input, an order in which the plurality of 2D ultrasound images are displayed.

16. The method of claim 13, wherein the displaying of the plurality of 2D ultrasound images comprises determining, based on a user input, an ultrasound image that is not to be displayed among the plurality of 2D ultrasound images.

17. The method of claim 13, wherein the plurality of 2D cross-sections are acquired by searching cross-sections respectively perpendicular to a first axis, a second axis, and a third axis with respect to the 3D ultrasound volume data regarding the region of interest, and
wherein the first through third axes are orthogonal to one another.

18. The method of claim 13, wherein the plurality of 2D cross-sections are acquired by searching cross-sections respectively parallel to a first axis, a second axis, and a third axis with respect to the 3D ultrasound volume data regarding the region of interest, and
wherein the first through third axes are orthogonal to one another.

19. The method of claim 13, wherein the determining of the priority levels of the plurality of 2D cross-sections comprises:
acquiring an area and a number of portions including the at least one feature in each of the plurality of 2D cross-sections; and
determining the priority levels of the plurality of 2D cross-sections based on at least one of the area and the number.

20. A computer program product comprising a non-transitory computer-readable recording medium having recorded thereon a program for executing the method of claim 13 on a computer.

21. An ultrasound diagnosis apparatus comprising:
a display;
a memory storing one or more instructions; and
at least one processor configured to execute the stored one or more instructions to:
acquire ultrasound image data regarding a region of interest of an object;
identify a first cross-section including at least one feature to be observed based on the ultrasound image data;
determine a priority level of the first cross-section based on the at least one feature included in the first cross-section and at least one feature in each of at least one previously identified cross-section; and
control the display to display, based on the priority level, a plurality of 2D ultrasound images respectively corresponding to at least some of the first cross-section and the at least one previously identified cross-section,
wherein the at least one feature to be observed comprises at least one of a shape, a texture, a propensity, and a characteristic portion of a tissue in the region of interest.

22. The ultrasound diagnosis apparatus of claim 21, wherein the at least one processor is further configured to execute the stored one or more instructions to:
acquire 3D ultrasound volume data based on the ultrasound image data; and
control the display to display a 3D ultrasound image obtained based on the 3D ultrasound volume data.

* * * * *